United States Patent [19]
Mezhinsky et al.

[11] Patent Number: 5,793,837
[45] Date of Patent: Aug. 11, 1998

[54] APPARATUS AND METHOD FOR X-RAY TOMOGRAPHY

[76] Inventors: Victor B. Mezhinsky, 740 N. Driftwood Ave., Brea, Calif. 92622-9023; Leonid Khiterer, 1381 S. Highland Ave., Fullerton, Calif. 92632

[21] Appl. No.: 385,680

[22] Filed: Feb. 8, 1995

[51] Int. Cl.⁶ .................................................. A61B 6/14
[52] U.S. Cl. .................................................. 378/38; 378/40
[58] Field of Search .......................................... 378/38–40

[56] References Cited

U.S. PATENT DOCUMENTS

| | | |
|---|---|---|
| 3,743,832 | 7/1973 | Wright . |
| 4,168,633 | 9/1979 | Ciavattoni et al. . |
| 4,599,739 | 7/1986 | Nishikawa et al. . |
| 4,646,335 | 2/1987 | Tammisalo et al. . |
| 4,661,967 | 4/1987 | Nishikawa . |
| 4,783,793 | 11/1988 | Virta et al. . |
| 4,852,134 | 7/1989 | Kinanen et al. . |
| 4,974,243 | 11/1990 | McArdle et al. . |
| 5,012,501 | 4/1991 | Palonen et al. . |
| 5,224,140 | 6/1993 | Virta et al. . |

Primary Examiner—Craig E. Church
Attorney, Agent, or Firm—Howard A. Kenyon

[57] ABSTRACT

Art abstract and method for X-ray tomography is disclosed. The apparatus moves the X-ray source in a complex motion with a simple mechanism that is both low cost and reliable. The patient must be positioned such that a straight line between the X-ray source and the film will always pass through the object to be X-rayed, regardless of the position of the X-ray source and the X-ray film which are in operative relationship to each other.

14 Claims, 3 Drawing Sheets

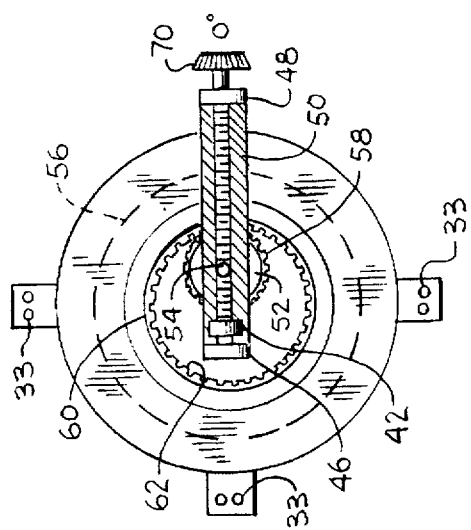
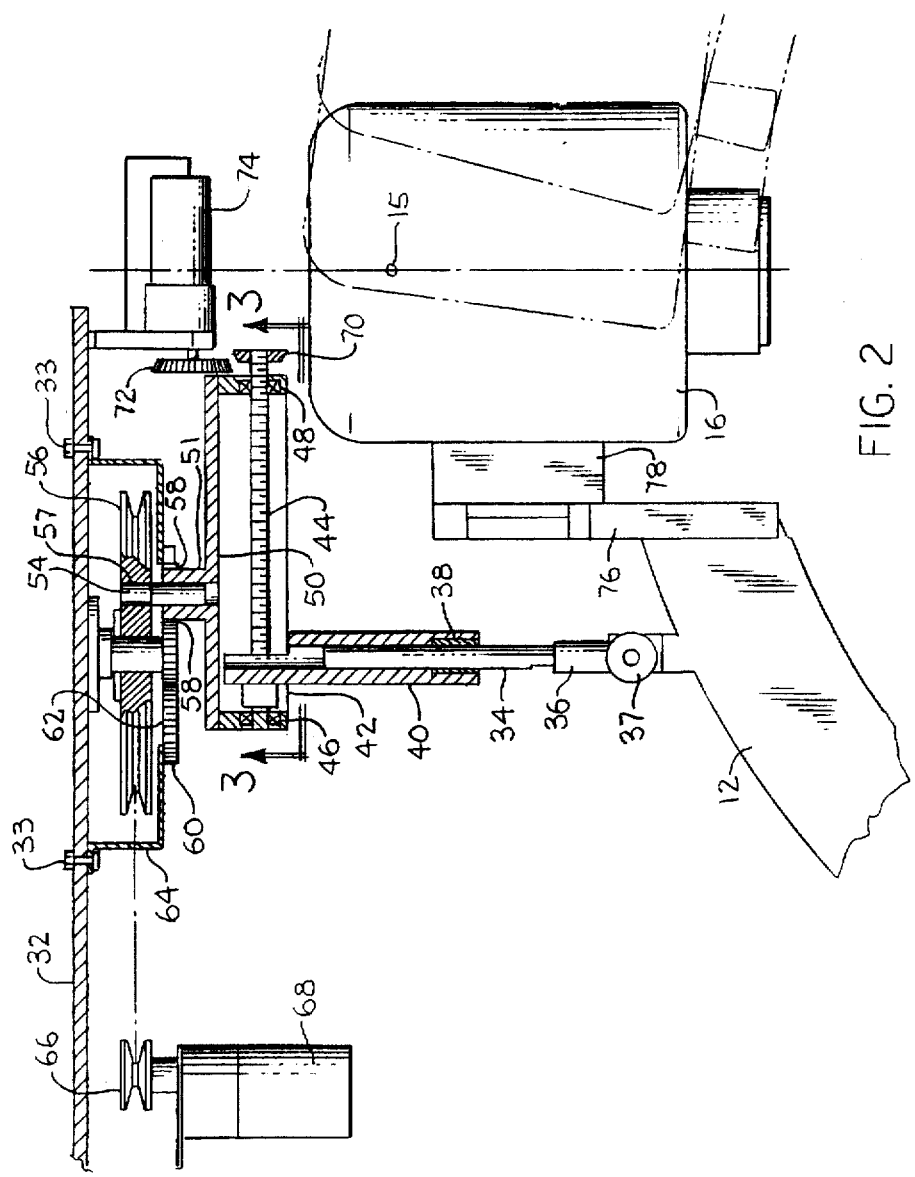
FIG. 3
FIG. 2

5,793,837

1

APPARATUS AND METHOD FOR X-RAY TOMOGRAPHY

BACKGROUND OF THE INVENTION

1. Field of the Invention

This invention relates to an apparatus and method for X-ray tomography and more specifically to a mechanical system to produce complex motions of the X-ray source.

2. Description of the Prior Art

There are numerous patents for obtaining tomographs in the dental, jaw and skull region to which the present invention is directed. One such patent is U.S. Pat. No. 4,852,134 to Kinamen et al which relates to a method and apparatus for the radiography of the dental, jaw and skull region.

Another reference is U.S. Pat. No. 4,646,335 to Tammisalo et al which uses a support arm that moves during the exposure of the film in a predetermined manner in such a way that this movement is dependent on the angular position of the support arm at each given time.

Still another reference is U.S. Pat. No. 4,599,739 to Nishikawa et al which is a dental apparatus for photographing the entire jaw. Many patents are directed to a panoramic dental X-ray machine. Patents for providing a panoramic X-ray image are: U.S. Pat. No. 4,168,633 to Ciavattoni et al; U.S. Pat. No. 5,012,501 to Palonen et al; U.S. Pat. No. 5,224,140 to Virta et al; U.S. Pat. No. 4,661,967 to Nishikawa and U.S. Pat. No. 4,738,793 to Virta et al.

All of the panoramic systems use a rotatable frame that has an X-ray source on one end and an X-ray film on the other end. The frame rotates around a stationary patient.

SUMMARY OF THE INVENTION

It is the object of the present invention to provide an apparatus and method for X-ray tomography.

It is another object of the present invention to provide a complex motion of the X-ray source.

It is still another object of the present invention to provide the complex motion with the combination of an electromechanical and mechanical devices.

Briefly, in accordance with the present invention, there is provided a commercially available X-ray source, an X-ray power controller, and an X-ray film cassette, an arm connecting the X-ray source and the X-ray film, an X-ray source electromechanical and mechanical drive mechanisms which produce the source complex motion, an arm supporting system which allows the support arm to rotate in both vertical and horizontal planes and an arm supporting structure. The present invention is used for, but not limited to, dental tomography. This includes the teeth, jaws, and skull region.

It is know that in order to produce a sharp image of the dental region, the support arm must move in a predetermined manner in such a way that this movement is dependent on the angular position of the support arm at any given time. The movement of the support arm which has attached the X-ray source and film produces the complex motion. The present invention provides the angular movement of the support arm with a combination of electromechanical and mechanical mechanisms.

DESCRIPTION OF THE DRAWINGS

In the drawings which illustrate the best mode presently contemplated for carrying out the present invention are:

2

Figure 1:
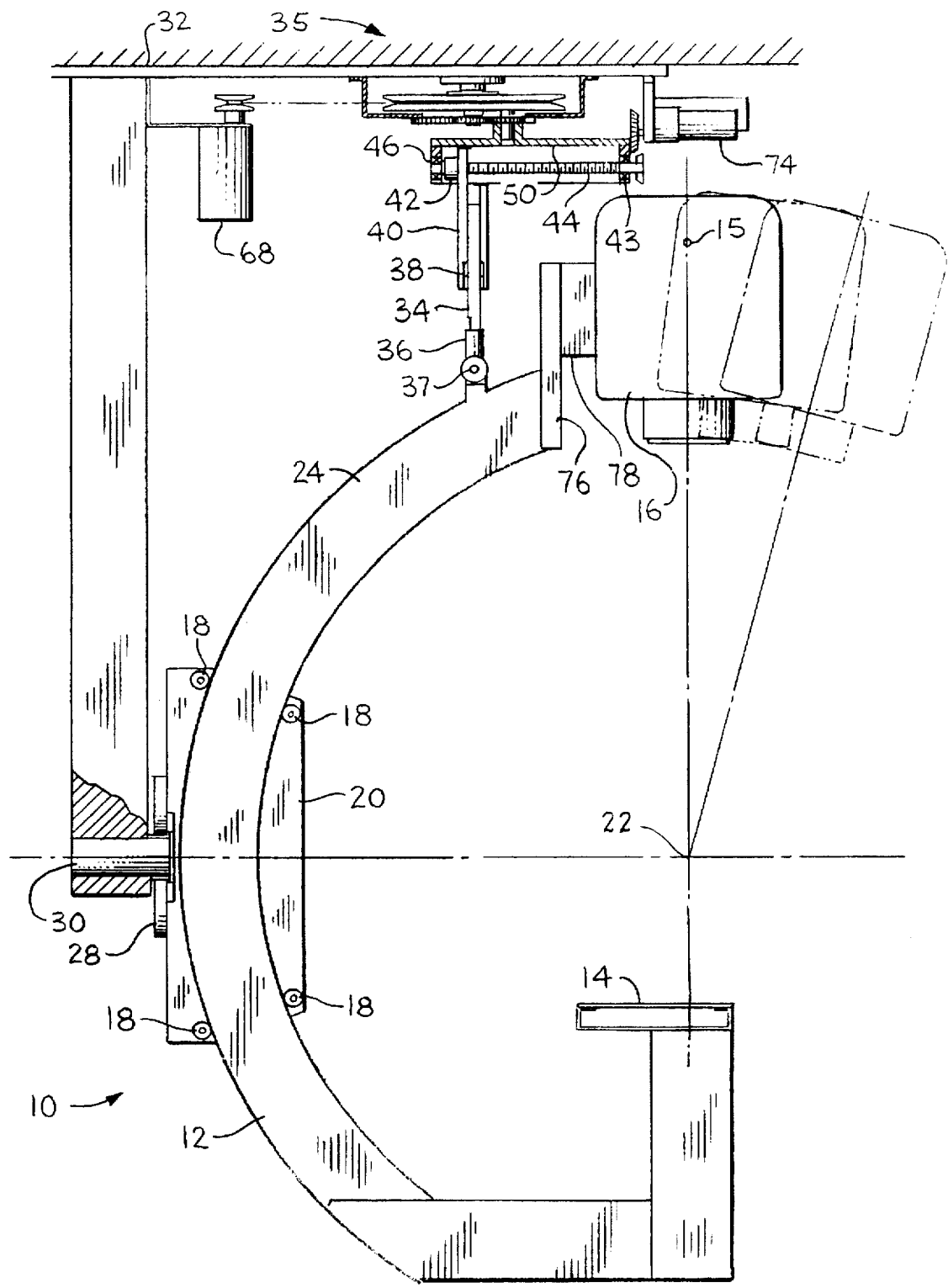

FIG. 1 is a partial side sectional view of the complete X-ray apparatus for providing complex motions of the X-ray source.

FIG. 2 is a detached partial side sectional view of the drive mechanism.

FIG. 3 is an end view of the drive mechanism that moves the X-ray source in a horizontal and vertical position.

Figure 4:
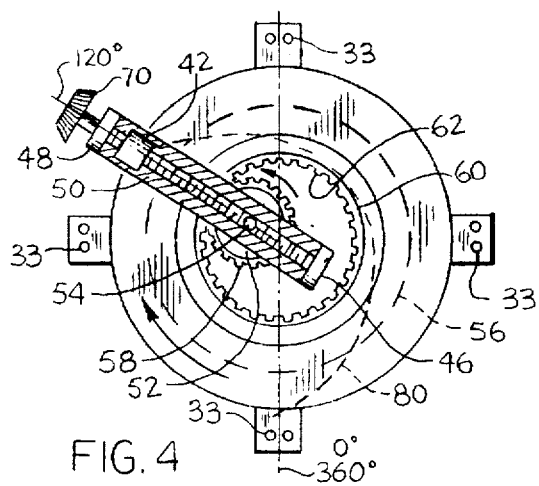

FIG. 4 is an end view of the attachment "c" shaped arm showing a first movement.

Figure 5:
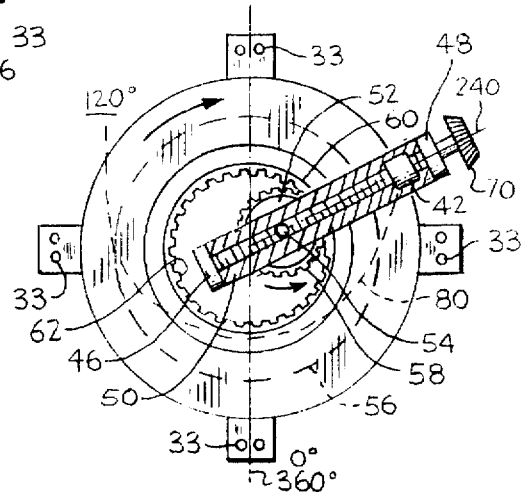

FIG. 5 is an end view of the attachment to the "c" shaped arm showing a second movement.

Figure 6:
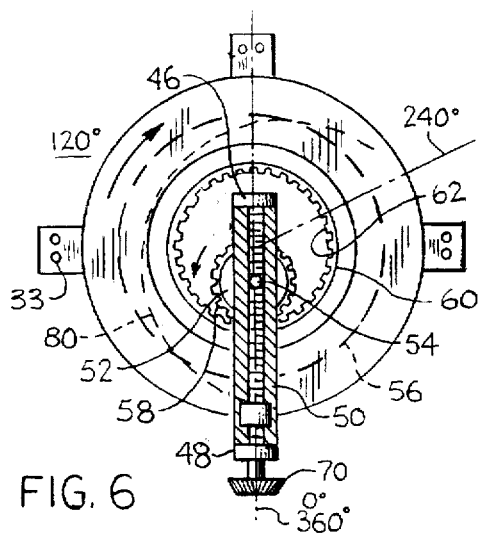

FIG. 6 is an end view of the attachment to the "c" shaped arm showing a third movement.

Figure 7:
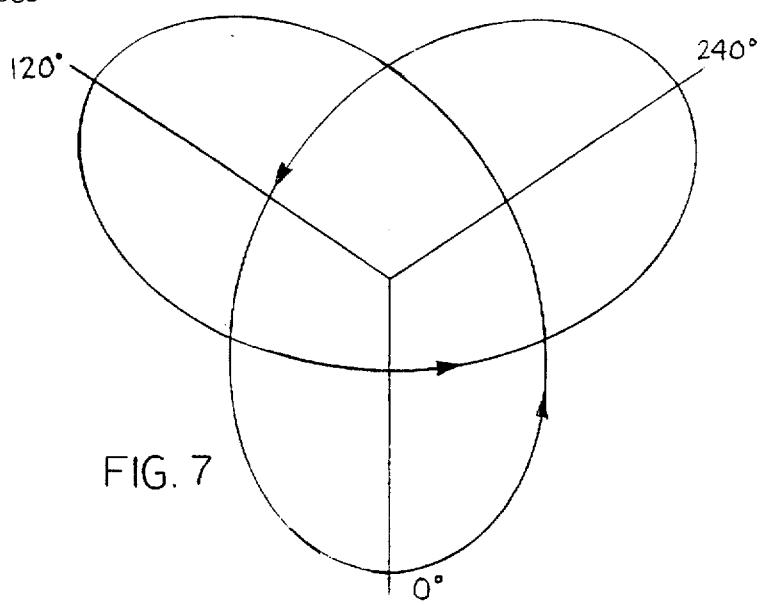

FIG. 7 shows a typical hypocycloid trace of the attachment to the "c" shaped arm.

These and other objects, features and advantages of the present invention will become more readily apparent upon detailed consideration of the following description of a preferred embodiment with reference to the accompanying drawings.

DETAILED DESCRIPTION OF THE INVENTION

Turning now to FIG. 1, there is seen an X-ray tomography apparatus generally shown as 10. Tomography apparatus 10 has a "c" shaped arm 12 having a film cassette 14 on one end and an X-ray source 16 on the other end. The center of the X-ray beam, called the focal spot 15, the center of the X-ray source 16, and the center of the film cassette 14 are in perfect alignment and the line between the two passes through the object to the X-rayed. This "c" shaped arm 12 is supported by four roller bearings 18 that are contained in housing 20. This allows the "c" shaped arm 12 to rotate around the center of a circle 22 formed by the surface 24 of the "c" shaped arm 12. In addition the X-ray source line 16 always passes through point 22 which is the detail of the teeth, jaw or skull region to be x-rayed. The housing 20 is pivotally attached to the beam 26 by a close tolerance bearing 28 and shaft 30. Beam 26 is further attached to plate 32 which is permanently attached to a wall 35 or a similar structure by fastening means (not shown). Plate 32 could be attached to a stand (not shown) to become a stand alone unit. A rod 34 has a self-aligning bearing 36 on one end. The self-aligning bearing 36 is a ball and socket configuration. The self-aligning bearing 36 has the outer race rigidly attached to the "c" shaped arm 12 by fastening means 37. The other end of rod 34 produced through a linear bearing 38 which is contained in a round housing 40. An internally threaded member 42 is rigidly attached to the top of the round housing 40. A threaded shaft 44 is supported on both ends by bearings 46 and 48 which are fitted into the ends of support structure 50. The threaded shaft 44 extends through round housing 40 to engage the internally threaded member 42.

Turning now to FIG. 2, support structure 50 has a support structure shaft housing 51 that is rigidly attached to a pinion gear 52 (as seen in FIG. 3). Shaft 54 attached to shaft housing 51 extends through pulley 56 which has a bearing 57 pressed therein. In FIG. 2 only the teeth 58 of pinion gear 52 can be seen. Further detailed of pinion gear 52 will be seen in FIG. 3. Pinion gear 52 and teeth 58 are engaged with ring gear 60 having internal teeth 62. Ring gear 60 is rigidly fixed to pulley housing 64 which is in turn fastened to plate 32 by fastening means 33. Pulley 56 contains a belt or chain (not shown) that engages pulley 66 on a electric motor 68 that is fastened to beam 26. On one end of threaded shaft 44, a friction wheel or gear 70 is attached thereon. The friction wheel or gear 70 is designed to engage friction wheel or gear 72 which is driven by electric motor 74 that is fastened to plate 32 by a fastening means (not shown). A solenoid (not shown) engages friction wheel or gear 72 with friction wheel or gear 70 when required. "c" shaped arm 12 is rigidly attached to X-ray source 16 by structures 70 and 78.

FIG. 4 shows the end view of the drive mechanism with the attachment to the "c" shaped arm moving through 240 degrees.

FIG. 5 shows the end view of the drive mechanism with the attachments to the "c" shaped arm moving through 240 degrees.

FIG. 6 shows the end view of the drive mechanism with the attachment to the "c" shaped arm moving through 240 degrees.

FIG. 7 shows a typical trace of the X-ray source complex motion which in this case is a hypocycloid. In order to accomplish a hypocycloid motion of the X-ray source, the pulley 56 must travel through one complete revolution of 360 degrees. Since the pulley 56 moves the pinion gear 52 around the fixed ring gear 60 which in turn moves support structure 50 which is attached to the pinion gear 52, this moves internally threaded member 42 in a complex motion. Since internally threaded member 42 is linked to the "c" shaped arm 12 and "c" shaped arm 12 is structurally attached to X-ray source 16, the X-ray source 16 also moves in a complex motion that is typical of that shown in FIG. 7.

FIG. 4, 5 and 6 accomplish a hypocycloid trace as shown in FIG. 7 with the X-ray source 16 at a specific angle with respect to a horizontal plane. Other positions of the X-ray source 16 may be obtained by activating a solenoid (not shown) when the support structure 50 is in its home or zero degree position as shown in FIG. 3. The solenoid moves friction wheel or gear 72 in contact with friction wheel or gear 70. Electric motor 74 is activated to rotate friction wheel or gear 72 which in turn rotates friction wheel or gear 70 when the friction wheels or gears are in contact. This in turn rotates threaded shaft 44 which moves internally threaded member 42 into a new position. This new position of internally threaded member 42 places the X-ray source 16 in a new position. When the correct position is obtained, the solenoid is deactivated and the electric motor 74 is turned off.

In the present invention the pulley 56 makes one complete revolution and returns to the home position as shown in FIG. 3. The pinion gear moves around the ring gear for one complete revolution. A design must be initiated to obtain this movement. The distance from the center line of the pulley 56 to the center line of the shaft 54 that is located in the face of the pulley 56, the diameter of the pinion gear 58, and the diameter of the ring gear 60, must be designed to obtain exactly one revolution of the pinion gear 58 around the ring gear and the movement of the support structure 50 and the internally threaded member 42 will provide a complex motion of the X-ray source 16.

The motion cycle begins with the operation depressing a switch (not shown) that energizes a preprogrammed electronic controller (not shown). A signal from the electronic controller engages electric motor 74 and solenoid which in turn engages friction wheels or gears 70 and 72. The electric motor 74 places the X-ray source 16 in the program position and the solenoid disengages friction wheels or gears 70 and 72. The controller, hereafter, engages the electric motor 68 to turn pulley 56 with a belt or chain. The turning of pulley 56 through one complete revolution provides a hypocycloid motion of the X-ray source 16. The position of the X-ray beam angle is directly related to the tomographic cut or thickness that may be viewed on the X-ray film.

It is well known in the x-ray art that equipment developed to produce a complex motion such as elliptical, FIG. 8, descending spiral or hypocycloidal instead of a linear motion, will produce images that have more effective blurring of unwanted structures.

The present disclosure includes that contained in the appended claims, as well as the forgoing description. Although this description has been described in its preferred form with a certain degree of particularity, it is understood that the present disclosure of the preferred form has been made only by way of example and that numerous changes in the details of construction and the combination and arrangement of parts may be resorted to without departing from the spirit and the scope of the invention.

What is claimed is:

1. An apparatus for x-ray tomography of the dental arch, the jaws and skull region, said apparatus comprising:

a rigid plate to fasten said apparatus;

a stationary frame, said stationary frame attached to said plate;

a housing connected to said frame by a bearing supported in said frame, said housing movable in a horizontal plane in relation thereto;

a C shaped arm supported by rollers on said housing, said C shaped arm rotatively movable in a vertical plane;

an x-ray source attached to said C shaped arm on one end;

a film cassette attached to C shaped arm on the other end, said x-ray source and said C shaped arm being in perfect alignment, and also having a beam from the x-ray source to the film cassette passing through the center of radius forming the C shaped arm, said beam from said x-ray source also passing through the object to be x-rayed;

means to move the ends of said C shaped arm in both horizontal and vertical planes simultaneously comprising:

a rod attached to said C shaped arm by a self aligning bearing on one end and a housing containing a linear bearing, said rod slidably position in said linear bearing on the other end;

an internal threaded member rigidly attached to one end of said housing;

a threaded rod perpendicular to said housing engaging said internally threaded member, said threaded rod being supported on each end by bearing means, said bearing means being located in a support structure connecting said bearing means, said threaded rod having a first friction wheel on one end.

2. An apparatus according to claim 1 wherein said threaded rod has a first gear on one end.

3. An apparatus according to claim 1 further comprising:

a shaft having a shaft housing attached to and perpendicular said support structure, said shaft housing having a pinion gear attached rigidly thereon;

a pulley, having a shaft with a fitted bearing on one end, said fitted bearing also attached to said rigid plate, said fitted bearing being concentric with the center of said rod attached to said "c" shaped arm;

a pulley housing rigidly attached to said rigid plate;

a ring gear rigidly attached to said pulley housing;

said shaft attached to said support structure and also having a pinion gear located on said shaft housing, said shaft extending through the fact of said pulley having bearing means in said face of said pulley.

4. An apparatus according to claim 3 where said pulley is rotated by said drive means from a pulley that is attached to a first electric motor.

5. An apparatus according to claim 4 wherein said drive means is a belt.

6. An apparatus according to claim 5 wherein the distance from the center line of said pulley to the center line of said shaft having a pinion gear attached thereon, the diameter of the pinion gear and the diameter of the ring gear must be such that one revolution of said pulley will result in said pinion gear making one revolution around said ring gear.

7. An apparatus according to claim 4 wherein said drive means is a chain.

8. An apparatus according to claim 4 further comprising:

a second electric motor having a shaft containing a second friction wheel;

a solenoid for moving said second friction wheel to engage said first friction wheel on the end of said threaded rod whereby engaging the two friction wheels turns said threaded rod and allows said internally threaded member to move and in turn shift x-ray source to a new position.

9. An apparatus according to claim 8 wherein said second electric motor has a shaft, said shaft containing a second gear;

a solenoid for moving said second gear to engage said first gear on the end of said threaded rod whereby engaging the two gears turns said threaded rod and allows said internally threaded member to move and in turn shift said X-ray source to a new position.

10. An apparatus according to claim 8 further comprising: switching means;

an electric controller for activating the first electric motor, the second electric motor and x-ray source.

11. An apparatus according to claim 10 wherein engaging switching means and said electronic controller results in the X-ray source being positioned at an angle of inclination with respect to a horizontal plane whereby engaging said first electric motor to drive said pulley will cause said X-ray source and said film cassette to provide a hypocycloid complex motion.

12. A method of X-ray topography of the dental arch, the jaws and skull region, said method comprising:

providing a stationary frame attached to a rigid plate;

providing a housing rotatively attached to said frame, said housing rotating in a horizontal plane;

providing a "c" shaped arm rotatively attached to said housing, said "c" shaped arm rotating in a vertical plane;

attaching an X-ray source on one end of said "c" shaped arm and a film cassette on the other end, said X-ray source and said film cassette being in perfect alignment;

moving said X-ray source such that said X-ray source is positioned at an angle of inclination with respect to a horizontal plane;

attaching a rod to said "c" shaped arm having a self aligning bearing on one end and a linear bearing on the other end, said linear bearing being fitted inside a round housing on one end, said round housing having an internally threaded member attached to said round housing on the other end, said internally threaded member having a threaded rod extending through said internal member and held in place by bearing means on the ends of said threaded rod, said bearing means being connected by a support structure, said threaded rod extending on one end with engaging means, said support structure having a shaft attached to and perpendicular to said support structure.

13. A method of X-ray topography of the dental arch, jaws and skull region according to claim 12, said method further comprising:

providing a first electric motor, said first electric motor having a pulley and belt attached thereto, providing a pulley housing having a shaft with a bearing on one end, said bearing being attached to said rigid plate, said pulley center being concentric with said rod center attached to said "c" shaped arm, said pulley having said belt attached thereon;

fitting a bearing in the face of said pulley, said bearing accommodating said shaft attached to said support structure, said shaft attached to a housing which is also attached to said support structure, said shaft housing having a pinion gear rigidly attached thereto;

providing a pulley housing rigidly attached to said rigid plate, said pulley housing having a ring gear rigidly attached, said ring gear having internal teeth accommodating said pinion gear external teeth;

providing a second electric motor having a shaft with engaging means thereon, said second electric motor having a solenoid to activate said engaging means;

rotating said pulley having a shaft fitted in said face until said engaging means on said second electric motor and said engaging means on the end of said threaded rod juxtraposed;

engaging said solenoid until both said engaging means are mated;

positioning said X-ray source until said X-ray source is at a specific angle of inclination with respect to a horizontal plane;

releasing said solenoid until said engaging means are separated.

14. A method of X-ray photography of the dental arch, the jaw and the skull region according to claim 13 wherein rotating said pulley containing said shaft in the face of said pulley, moves said pinion gear around said ring gear whereby said "c" shaped arm having said X-ray source attached thereto is moved through a hypocycloid motion.

* * * * *